US006211477B1

(12) United States Patent
Cardott et al.

(10) Patent No.: US 6,211,477 B1
(45) Date of Patent: Apr. 3, 2001

(54) ELECTROSTATIC DECELERATION SYSTEM FOR FLOW CYTOMETER

(75) Inventors: John N. Cardott, Morgan Hill, CA (US); Larry D. Duckett, Chester, MD (US); Carleton C. Stewart, Orchard Park, NY (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/030,928

(22) Filed: Feb. 26, 1998

(51) Int. Cl.[7] ........................................... B03C 7/00
(52) U.S. Cl. .................. 209/127.4; 209/3.1; 209/128; 436/50
(58) Field of Search ..................... 209/3.1, 3.2, 127.1, 209/127.4, 130, 128; 436/43, 50, 164

(56) References Cited

U.S. PATENT DOCUMENTS

| | | | |
|---|---|---|---|
| 4,230,031 | 10/1980 | Pedroso et al. | 209/3 X |
| 4,347,935 | 9/1982 | Merrill | 209/3.2 |
| 5,030,002 | 7/1991 | North, Jr. | 209/3.1 X |
| 5,150,313 | 9/1992 | van den Engh et al. | 364/569 |
| 5,188,935 | 2/1993 | Leif et al. | 435/7.24 |
| 5,454,472 | 10/1995 | Benecke et al. | 209/127.1 |
| 5,464,581 | 11/1995 | van den Engh | 422/82.01 |
| 5,466,572 | 11/1995 | Sasaki et al. | 435/2 |
| 5,475,487 | 12/1995 | Mariella, Jr. et al. | 356/336 |
| 5,483,469 | 1/1996 | Van den Engh et al. | 364/555 |
| 5,489,506 | 2/1996 | Crane | 209/127.4 X |
| 5,570,736 | 11/1996 | Nara et al. | 164/466 |
| 5,602,039 | 2/1997 | Van den Engh | 209/127.4 X |
| 5,602,349 | 2/1997 | Van den Engh | 73/864.85 |
| 5,627,037 | 5/1997 | Ward et al. | 73/864.85 |
| 5,627,040 | 5/1997 | Bierre et la. | 435/7.24 |
| 5,643,796 | 7/1997 | Van den Engh et al. | 209/4 X |
| 5,944,875 | * 8/1999 | Stencel et al. | 209/127.4 X |

FOREIGN PATENT DOCUMENTS

| | | | |
|---|---|---|---|
| 1114472 | * 9/1984 | (SU) | 209/127.1 |

OTHER PUBLICATIONS

FACSort™ Brochure, Becton Dickinson and Company, 1994.

FACSCount™ Brochure, Becton Dickinson and Company, 1994.

FACScan™ Brochure, Becton Dickinson and Company, 1994.

FACS Vantage™ Brochure, Becton Dickinson and Company, 1995.

FACSCalibur™ Brochure, Becton Dickinson and Company, 1995.

FACS Loader™ Brochure, Becton Dickinson and Company, 1995.

* cited by examiner

Primary Examiner—Tuan N. Nguyen

(57) ABSTRACT

An electrostatic deceleration system is provided for use with a flow cytometer to decelerate the movement of electrically charged droplets formed by the flow cytometer in order to minimize damage to the cells contained in the droplets when the droplets are collected in corresponding collection vessels. The deceleration system includes a plurality of deceleration devices which are each used to decelerate droplets charged to a particular magnitude and polarity. Each deceleration device includes a steering plate arrangement and a deceleration ring arrangement. The steering plate arrangement directs the droplets having a particular magnitude and polarity of charge into the corresponding deceleration ring arrangement. The deceleration ring arrangement includes a plurality of deceleration rings to which are applied electrical potentials of a polarity the same as the polarity of the charged droplet. These potentials apply an electrostatic force gradient to the droplet as it passes through the rings, and thus reduce the speed at which the droplet travels. As the droplets passing through the deceleration ring arrangement are slowed, the droplets reform into a continuous stream prior to entering a collection vessel where the cells contained in the droplets are collected.

33 Claims, 7 Drawing Sheets

ELECTROSTATIC DECELERATION SYSTEM FOR FLOW CYTOMETER

BACKGROUND OF THE INVENTION

The present invention relates to a device which is adaptable for use with a flow cytometer to decelerate electrically charged droplets formed by the flow cytometer, in order to minimize damage to the cells contained in the droplets when the droplets are collected in corresponding collection vessels. More particularly, the device includes a plurality of deceleration devices arranged in correspondence with the collection vessels into which charged droplets traveling along different paths in a flow cytometer are collected, with each deceleration device creating an electrostatic field which repels and thus slows the movement of the droplets so that the droplets enter the corresponding collection vessels at reduced speeds.

Flow cytometers for sorting and examining biological cells are well known in the art. Known flow cytometers are described, for example, in U.S. Pat. Nos. 4,347,935, 5,464,581, 5,483,469, 5,602,039 and 5,643,796, the entire contents of which are incorporated by reference herein. Another known flow cytometer is the FACS Vantage™ system manufactured by Becton Dickinson and Company, the assignee of the present invention. A flow cytometer typically includes a sample reservoir for receiving a biological sample, such as a blood sample. The sample contains cells that are to be analyzed and sorted by the flow cytometer.

Physical and fluorescent properties of particles hereinafter called cells can be measured as they intersect a laser beam. This is accomplished by transporting cells in a cell stream to a flow cell. Within the flow cell, a liquid sheath is formed around the cell stream to impart a uniformly velocity and to hydrodynamically focus the cells within the stream onto the center of a laser beam. The point of intersection or interrogation point can be inside or outside the flow cell. As a cell moves through the interrogation point, it causes the laser light to scatter and fluorescent molecules either within the cell or added to the cell becomes excited.

An appropriate detection system consisting of photomultipliers tubes, photodiodes or other devices for measuring light are focused onto the intersection point where the properties are measured. To sort cells by an electrostatic method, the desired cell must be contained within an electrically charged droplet. To produce the droplet, the flow cell is rapidly vibrated by an acoustical device. These droplets form after the cell stream exits the flow cell and at a distance from the interrogation point so that a time delay is required between the interrogation point and the actual break off point of the droplet. This time delay is determined by appropriately designed electronic circuits that are synchronized with the device that forms the droplets.

To charge the droplet, the cell stream passes by or through a charging power whose electrical potential relative to a charge generated in the sheath fluid can be rapidly changed. At the instant the desired cell is in the droplet just breaking away from the cell stream, the charging power is brought up to potential thereby causing the droplet to isolate the charge once broken off from the stream. The electrostatically charging device can cycle to appropriately charge each droplet as it is being broken off the cell stream.

Because the cell stream exits the flow cell in a substantially downward vertical direction, the droplets also propagate in that same direction after they are formed. To sort the charged droplet containing the desired cell, they are deflected from the trajectory of uncharged droplets as they pass through an electrostatic field formed by two deflection plates held constant at a high electrical potential difference. Positively charged droplets are attracted by the negative plate and repelled by the positive plate while negatively charged droplets are attracted to the positive plate and repelled by the negative plate. This causes their trajectory to become changed thereby sorting them from other cells. Because of their high velocity and because of the length of the plate, the cells clear the deflection field before striking the deflection plates. Accordingly, the droplets in the cells contained therein can be collected in their appropriate collecting vessels.

Although flow cytometers of the type described above are generally effective in sorting and analyzing cells, the speed at which these systems can operate is limited by the physical fragility of the cells. That is, to increase the rate at which the droplets are formed, analyzed and sorted, it is necessary to increase the pressure in the sheath fluid to thereby increase the flow rate of the fluid jet. Although some flow cytometers are capable of performing the required analyzing and sorting operations as the droplet flow rate is increased, the increased velocity of the droplets can result in the droplets striking the interior of the collection vessels with a force sufficient to damage or rupture the cells contained in the droplets. Typically, a sheath fluid pressure of greater than 40 psi will cause the droplets to be ejected from the nozzle at a speed great enough to cause damage to the cells when the droplets strike the interior of the collection vessels. By maintaining the pressure of the sheath fluid below these levels to avoid damage to the cells, it is not possible to sort cells at interrogation rates greater than about 2,000 cells per second.

Accordingly, a need exists for a flow cytometer which is capable of operating at an increased droplet flow rate while avoiding damage to the cells contained in the droplets.

SUMMARY OF THE INVENTION

An object of the present invention is to provide a droplet deceleration device, adaptable for use with a flow cytometer, which decelerates the droplets prior to their entry into their respective collection vessels to reduce the impact of the droplets against the vessel walls, thus avoiding damage to the cells contained in the droplets.

Another object of the invention is to provide a droplet deceleration device with an electrostatic field generating device which generates an electric field to repel the charged droplets and thereby decelerate the charged droplets prior to their entry into their respective collection vessels.

A further object of the invention is to provide a droplet deceleration device with steering plates which create an electrostatic field that influences the path along which the charged droplets travel to assist in guiding the charged droplets into the electrostatic field generating device which decelerates the droplets.

A still further object of the invention is to provide an electrostatic field generating device as a plurality of split or solid rings that are stacked in succession with their central axes in substantial alignment, and to which are applied electrical potentials having a polarity the same as that of the charged droplet, thereby exerting electrostatic forces on the droplets to slow the speed of the charged droplet in increments corresponding to the ring potentials.

A still further object of the invention is to provide a movable electrostatic field generating device which can be aligned with different paths along which the charged droplets can travel, so that the device is capable of decelerating charged droplets traveling on any of several different paths.

These and other objects of the invention are substantially achieved by providing a device, adaptable for use with a flow cytometer, for influencing the movement of an electrically charged droplet that has passed through an electrostatic field generated by the flow cytometer. The device comprises a conductive element system which is disposed at a location traversed by the droplet after the droplet passes through the electric field, and a potential source which applies an electrical potential to the conductive element system, thereby influencing the movement of the droplet when the droplet traverses the conductive element system.

The conductive element system can include sets of conductive elements which each include one or more steering plates and a plurality of deceleration rings. A potential source applies an electrical potential to the steering plates which influences the path along which the charged droplet travels to assist in directing the charged droplet into the corresponding deceleration rings. The potential source also applies to the deceleration rings potentials of different levels at a polarity the same as that of the charged droplet to repel the charged droplet and thus decelerate the movement of the charged droplet prior to its entry into a collection vessel. The positions of the sets of steering plates and deceleration rings can be adjusted as desired to align with different paths along which the charged particles may travel.

BRIEF DESCRIPTION OF THE DRAWINGS

The various objects, advantages and novel features of the present invention will be more readily appreciated from the following detailed description when read in conjunction with the accompanying drawings, in which.

Throughout the drawings, like reference numerals will be understood to refer to like parts and components.

DETAILED DESCRIPTION OF THE PREFERRED EMBODIMENTS

Figure 1:
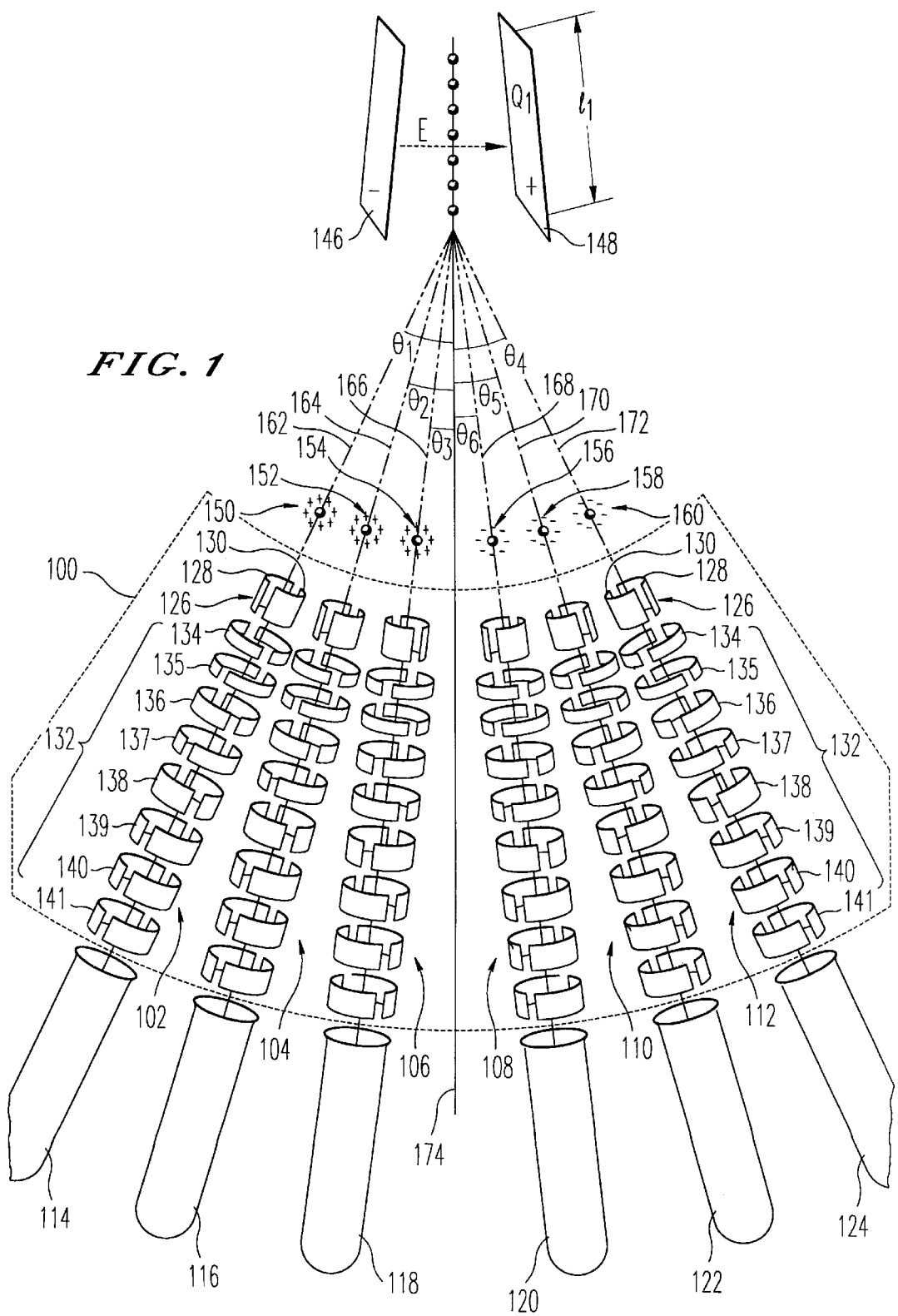
FIG. 1 is a schematic illustration of an electrostatic deceleration system according to an embodiment of the present invention which is adaptable for use with a flow cytometer.
Figure 2:
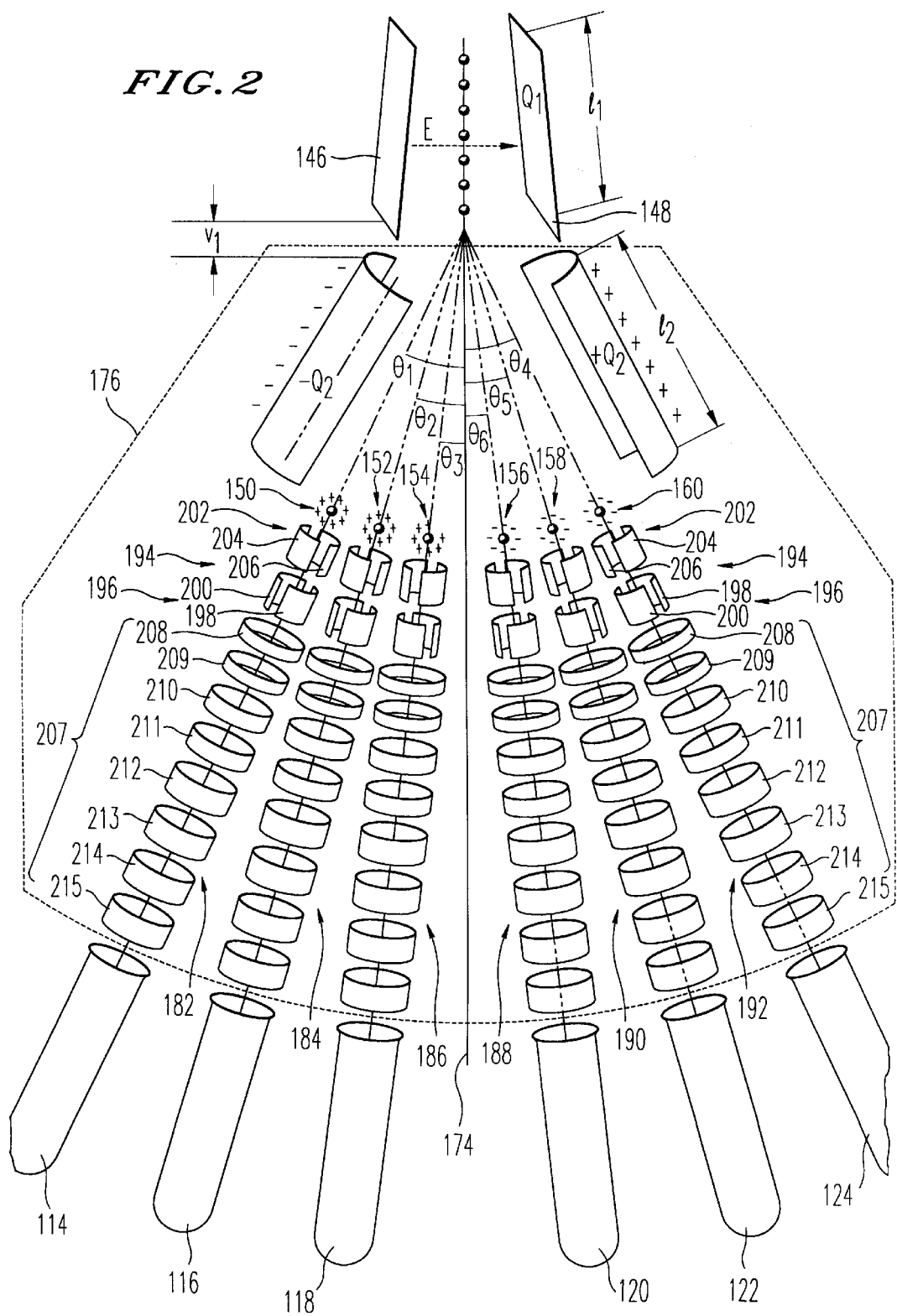
FIG. 2 is a schematic illustration of an electrostatic deceleration system according to another embodiment of the present invention, which includes modifications to the embodiment shown in FIG. 1.

Two embodiments of an electrostatic deceleration system according to the present invention are illustrated schematically in FIGS. 1 and 2. As shown in FIG. 1, the deceleration system 100 includes a plurality of deceleration element sets 102, 104, 106, 108, 110 and 112. Although in this example, the deceleration system 100 includes six deceleration element sets 102–112, any number of deceleration element sets can be employed in a deceleration system 100. Specifically, the number of deceleration element sets in the deceleration system 100 should correspond to the maximum number of collection vessels that can be used in the flow cytometer. In this example, the flow cytometer includes six collection vessels 114, 116, 118, 120, 122 and 124, and accordingly, six corresponding deceleration element sets 102–112.

As further illustrated in FIG. 1, each deceleration element set 102–112 includes a steering plate arrangement 126 whose purpose is described in more detail below. In this example, each steering plate arrangement 126 includes two steering plates 128 and 130 which are each made of a conductive material such as copper or any other suitable metal. However, as is described in more detail below, the steering plate arrangement 126 can in some embodiments include only one steering plate 128 or 130. For convenience, only the steering plate arrangements 126 of deceleration element sets 102 and 112 are numbered.

As further shown, each deceleration element set 102–112 further includes a deceleration ring arrangement 132. The deceleration ring arrangement 132 in each deceleration element set 102–112 includes a plurality of deceleration rings 134, 135, 136, 137, 138, 139, 140 and 141, which are arranged so that their axes are aligned or essentially aligned with each other as indicated. For convenience, only the deceleration ring arrangements 132 of deceleration element sets 102 and 112 are numbered. As described in more detail below, the deceleration rings 134–141 are made of an electrically conductive material, such as copper or any other suitable metal. As further illustrated, the height of the deceleration rings 134–141 can vary as desired. Furthermore, in this example, the deceleration rings 134–141 are of a split-ring configuration having two sections that are separated from each other by a desired distance. Also, as can be appreciated from the description below, although this example shows the deceleration ring arrangements 132 as each including 8 deceleration rings 134–141, the number of deceleration rings can be varied as desired.

As further illustrated, the deceleration system 100 is arranged in a flow cytometer at a location below the charged plates 146 and 148 of the flow cytometer. The deceleration system receives charged droplets that have passed through the electric field E generated between the plates 146 and 148. As described in the background section above, the flow cytometer performs a cell sorting function by applying a particular charge to a sheath fluid droplet containing a cell being examined. The electrostatic field generated between the plates 146 and 148 causes the charged droplet to be deflected by an amount proportionate to the amount of charge on the droplet. Also, the polarity of charge on the droplet will determine whether the droplet is deflected in a direction toward the positively charged plate 148 or toward the negatively charged plate 146.

Accordingly, as shown in the example of FIG. 1, the flow cytometer system deflects charged droplets 150, 152, 154, 156, 158 and 160 so that those charged droplets are caused to travel along corresponding paths 162, 164, 166, 168, 170 and 172, respectively, to be received in corresponding collection vessels 114, 116, 118, 120, 122 and 124, respectively. Hence, charged droplet 150, which has the greatest positive charge of all the droplets, is directed along path 162 which is at an angle θ1 with respect to the center line 174. Charged droplet 152, which has a lesser positive charge than charged droplet 150, is directed along path 164, which is at an angle θ2 with respect to center line 174. As shown, angle θ1 is greater than angle θ2, because a charged droplet 150 having a greater positive charge will be attracted with greater force toward the negatively charged plate 146 than a droplet 152 having a lesser positive charge. Accordingly, the deflection of charged droplet 150 in the direction toward negatively charged plate 146 is the greatest.

On the other hand, charged droplet 160 has the greatest negative charge of all the droplets, and thus will be deflected to travel along path 172, which is at an angle θ4 from center line 174. Charged droplet 158, which has a lesser negative charge, is deflected to travel along path 170 which is at an angle θ5 with respect to the center line 174. As shown, angle θ4 is greater than angle θ5, indicating that the charged droplet 160 having the greatest negative charge is most attracted to the positively charged plate 148, and thus deflected at the greatest angle from center line 174. Because charged droplets 154 and 156 have the smallest positive and negative charges, respectively, they are deflected to travel along paths 166 and 168, which are at the smallest relative angles θ3 and θ6 from center line 174.

As is described in more detail below, when the charged droplets 150–160 travel along paths 162–172 they enter a corresponding steering plate arrangement 126. Each steering plate arrangement 126 generates an electrostatic force that is applied to a charged droplet when the charged droplet passes through the steering plate arrangement 126. The electrostatic force acts on the charged droplet to adjust the path of travel of the droplet as necessary so that the charged droplet will enter the corresponding deceleration ring arrangement 132 at the center or essentially at the center of the uppermost deceleration ring 134. The electrostatic force produced by the steering plate arrangement also prevents the charged droplet from being repelled or deflected out of the deceleration ring arrangement 132 due to the repulsive electrostatic force applied to the charged droplet by the deceleration ring arrangement 132.

As described in more detail below, potentials of increasing magnitude are applied to the successive deceleration rings 134–141 of each deceleration ring arrangement 132. The applied potentials have a polarity that is the same as the polarity of the charged droplet. For instance, negative potentials are applied to the deceleration rings 134–141 of the deceleration ring arrangements 132 associated with paths 168, 170 and 172 along which negatively charged droplets 156, 158 and 160 travel. On the other hand, positive potentials are applied to the deceleration rings 134–141 of the deceleration ring arrangements 132 associated with paths 162, 164 and 166, along which positively charged droplets 150, 152 and 154 travel.

The potentials applied to the deceleration rings 134–141 produce electrostatic forces on the charged droplet as the charged droplet passes through the openings in the deceleration rings 134–141. These electrostatic forces repel the charged droplet and thus decreases the speed at which the charged droplet travels. The larger potentials apply larger electrostatic forces to the charged droplet, and therefore decelerate the charged droplet by a proportionately larger amount.

As the charged droplets are decelerated in their respective deceleration ring arrangements 132, the charged droplets traveling along each respective path 162–172 begin to recombine with the other charge droplets traveling along those paths, which are also being decelerated by the corresponding deceleration ring arrangements 132. Hence, the decelerated charged droplets begin to reform into a continuous sheath fluid stream containing the cells previously contained in the individual charged droplets.

After the charged droplets which have begun to reform into a sheath fluid stream exit the corresponding deceleration ring arrangement 132, the sheath fluid and cells will enter the corresponding collection vessel 114–124. Because the speed at which the fluid and cells are entering the vessels 114–124 has been reduced by the deceleration ring arrangements 132, the cells will strike the interior surfaces of the collection vessels 114–124 with a reduced force. Accordingly, the cells will not rupture or otherwise be damaged as they strike the interior surfaces of the collection vessels 114–124.

Although it is desirable for the deceleration rings 134–141 of the deceleration ring arrangements 132 to be of a split-ring configuration as shown in FIG. 1, the deceleration rings can instead consist of solid rings as shown in the deceleration system 176 of FIG. 2. The deceleration system 176 is similar to the deceleration system 100 of FIG. 1, but includes several modifications. Specifically, the deceleration system 176 includes a negatively charged curved plate 178 and a positive charged curved plate 180 which are disposed below the charged plates 146 and 148 of the flow cytometer. An additional electrostatic field is generated between curved plates 178 and 180 to further influence the deflection of charged droplets 150–160. The curvature of the charged plates 178 and 180 creates a more centrally localized electrostatic field which deflects the charged droplets 150–160 in a more controlled manner than charged plates 146 and 148.

As further shown in FIG. 2, the deceleration system 176 includes deceleration element sets 182, 184, 186, 188, 190 and 192, each of which includes a steering plate arrangement 194. As shown, the steering plate arrangement 194 includes a first pair 196 of steering plates 198 and 200 and a second pair 202 of steering plates 204 and 206. Each pair 196 and 202 of steering plates is similar to the single pair of steering plates 128 and 130 shown in FIG. 1. However, these two pairs 196 and 202 of steering plates are arranged so that their central axes are aligned with or substantially aligned with each other as shown. For convenience, only the steering plate arrangements 194 of deceleration element sets 182 and 192 are numbered. Also, as discussed above with regard to FIG. 1, the steering plate arrangement 194 need not include first and second pairs 196 and 202 of steering plates, but rather, two single steering plates (e.g., steering plates 198 and 204 or steering plates 200 and 206). The steering plate arrangement 126 in the deceleration system 100 of FIG. 1 can also include multiple pairs of steering plates.

As further illustrated in FIG. 2, each deceleration element set 182–192 of the deceleration system 176 includes a deceleration ring arrangement 207, comprising deceleration rings 208, 209, 210, 211, 212, 213, 214, and 215, which are made of an electrically conductive material such as copper or any other suitable metal. However, unlike the deceleration rings 134–141 in the deceleration system 100 shown in FIG. 1, the deceleration rings 208–215 are solid rings that are stacked in succession with their central axes aligned with or essentially aligned with each other. For convenience, only the deceleration ring arrangements of deceleration elements sets 182 and 192 are numbered.

The details of the steering plate arrangements and deceleration rings, and the deceleration systems 100 and 176, as a whole, will now be described in more detail with regard to FIGS. 3A through 9.

Figure 3A:
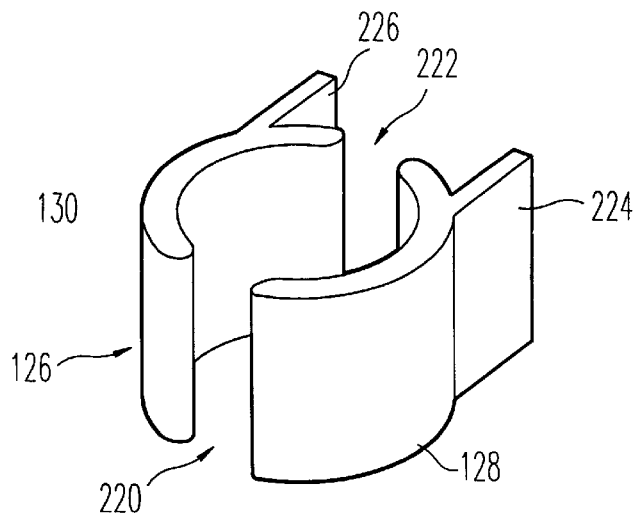
FIG. 3A is a detailed perspective view of the steering plates be used in the deceleration system shown in FIGS. 1 and 2.

FIG. 3A is a detailed perspective view of a steering plate arrangement 126 as described above, which is representative of a typical steering plate pair arrangement employed in the deceleration systems 100 and 176. As shown, steering plates 128 and 130 can be the same or essentially the same height and thickness. The steering plates 128 and 130 are curved and are spaced from each other by spaces 220 and 222. The steering plates 128 and 130 can have, for example, a height of about 0.75 inches, a thickness of about 0.125 inches, and an overall length of about 0.75 inches so that when they are arranged as shown in FIG. 3A, they form a circle having a radius of about 0.3 inches. The spaces 220 and 222 can vary in proportion to the size of the steering plates 128 and 130, and are typically in the range of up to about 0.5 inches. All of these values, however, are application dependent and thus, the steering plates 128 and 130 can have any suitable size and be spaced from each other by any suitable distance.

Figure 3B:
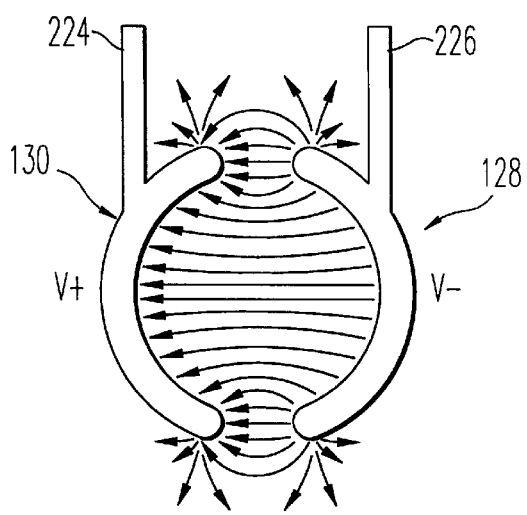
FIG. 3B is a top view of the steering plates shown in FIG. 3A, illustrating the electrostatic field lines generated between the steering plates.

As further shown in FIGS. 3A and 3B, the steering plates 128 and 130 include respective leads or connector portions 224 and 226 which have any suitable length. As described in more detail below, these leads 224 and 226 can be coupled to potential sources which apply voltages having a negative or positive polarity to the steering plates as desired. As shown in FIG. 3B specifically, in this example, a positive voltage V+ is applied to steering plate 130 via lead 226, and a negative voltage V− is applied to steering plate 128 via lead 224. These positive and negative voltages V+ and V− create an electric field $E_a$ between steering plates 128 and 130 as shown specifically in FIG. 3B. The significance of this electric field $E_a$ is discussed in further detail below.

Figure 4A:
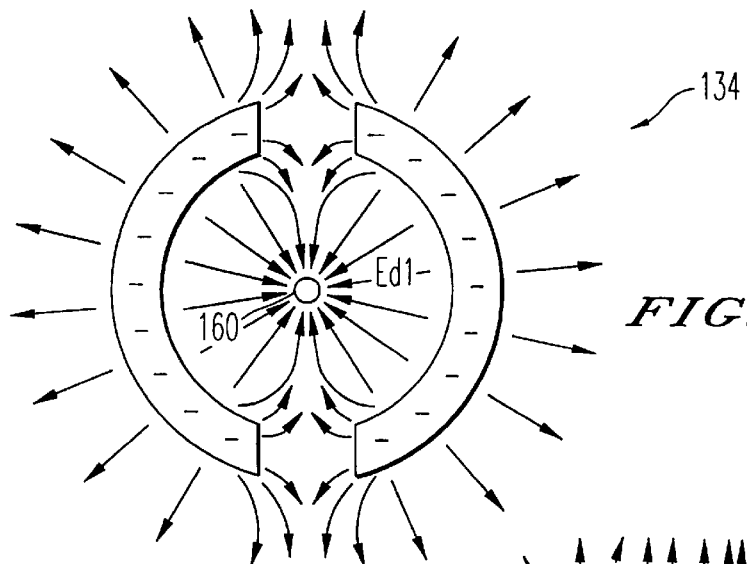
FIG. 4A is a top view of a split deceleration element used in the deceleration system of FIG. 1, showing the electrostatic field lines generated by the deceleration ring when a charged droplet is present.
Figure 4B:
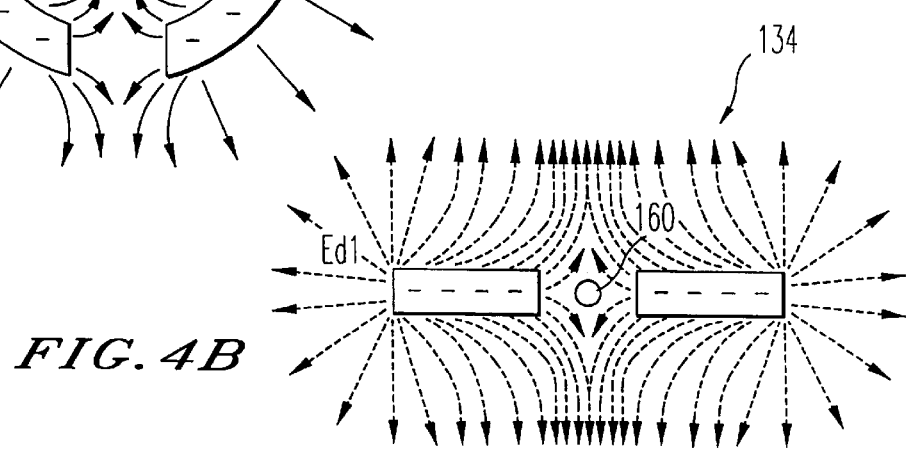
FIG. 4B is a side view of the split-ring deceleration element shown in FIG. 4A, illustrating the electrostatic field lines acting on a charged droplet.

An example of a deceleration ring 134 having a split-ring configuration is shown in FIGS. 4A and 4B. The deceleration rings can have, for example, a height within a range of about 0.25 inches to about 1.0 inch, and the split-ring portions can have a length and be spaced from each other to form a ring having a radius of about 0.5 inches. However, as with the steering plates 128 and 130, the sizes of the deceleration rings are application dependent and thus, the split ring sections can have any suitable thickness, length and height and can be spaced from each other by any suitable distance. As indicated, and as described in more detail below, a potential source applies a voltage of a particular polarity to the deceleration ring 134. In this example, the voltage has a negative polarity. However, as explained in more detail below, the applied voltage can be either positive or negative, as long as it is the same as the polarity of the charge on the charged droplet.

FIGS. 4A and 4B further illustrate examples of electrostatic fields lines $E_{d1}$ that are created when a charged droplet (e.g., charged droplet 160) is present at the center or essentially at the center of the deceleration ring 134. As described in more detail below, this electrostatic field has a repelling effect on the charged droplet 160, which influences the speed at which the charged droplet 160 travels.

Figure 5A:
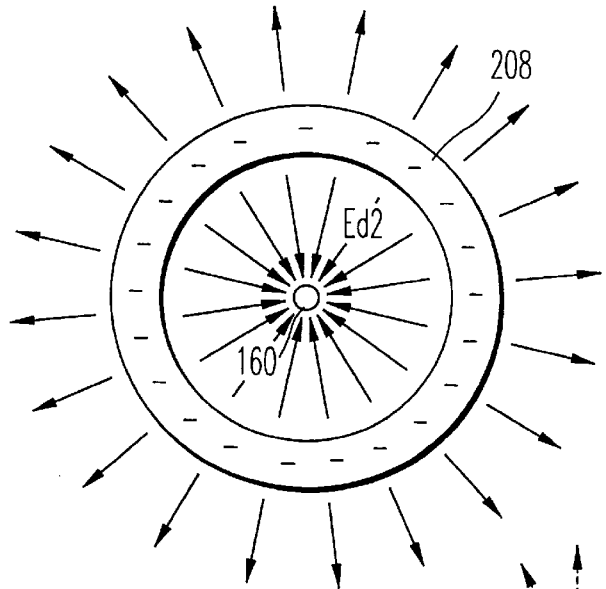
FIG. 5A is a top view of a solid-ring deceleration element used in the deceleration system of FIG. 2, illustrating the electrostatic field lines generated by the deceleration ring when a charged droplet is present.
Figure 5B:
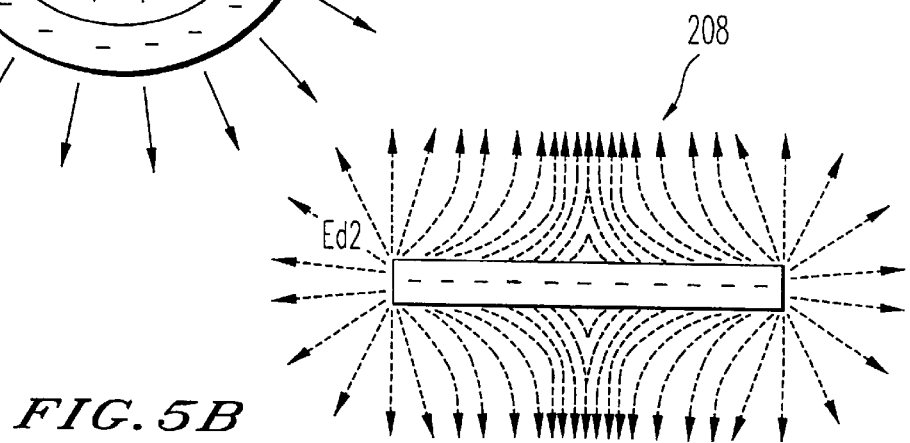
FIG. 5B is a side view of the solid-ring deceleration element shown in FIG. 5A, illustrating the electrostatic field lines acting on a charged droplet.

FIGS. 5A and 5B illustrate an example of a deceleration ring 208 having a solid ring configuration as described above. As with the deceleration ring 134, these solid rings can have any suitable thickness, circumference and height depending on their intended use. A potential is applied to the deceleration ring 208. In this example, the applied potential has a negative polarity, but the applied potential can have either a positive or negative polarity as long as its polarity is the same as the polarity of the charged droplet passing through the ring 208. As further illustrated, this negative voltage potential creates an electric field $E_{d2}$ when a charged droplet (e.g., charged droplet 160) is present in the center of ring 208. As described in more detail below, this electrostatic field exerts a repelling force on charged droplet 160 to decrease the speed at which the charged droplet 160 travels.

Figure 6:
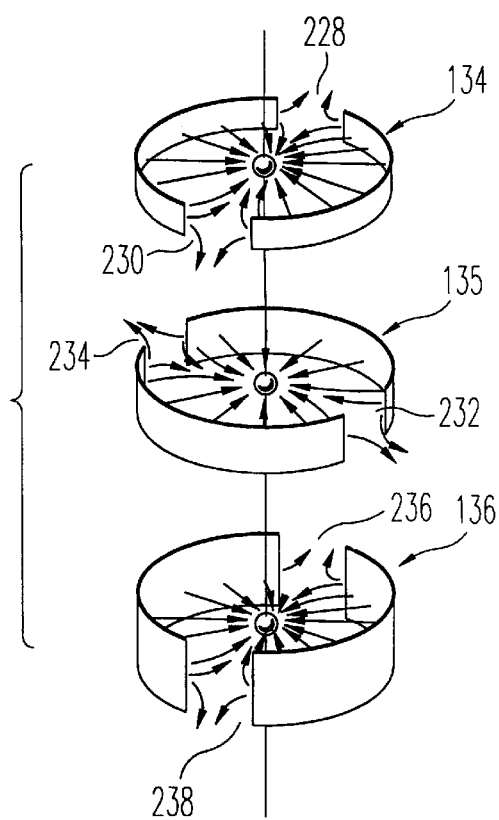
FIG. 6 is a schematic illustration of a stacked arrangement of the split-ring deceleration elements and their respective electrostatic field lines acting on respective charged droplets.

Although the deceleration rings can have a split-ring configuration or solid-ring configuration as described above, it is preferable that the deceleration rings have a split-ring configuration. However, when the deceleration rings having a split-ring configuration are arranged in a deceleration ring arrangement, such as deceleration ring arrangement 132 of deceleration system 100 as shown in FIG. 1, it is desirable that the spaces between the ring sections in adjacent deceleration rings are oriented at 90° (or about 90° ) from each other. This orientation is shown in FIG. 6, which illustrates the first three deceleration rings 134, 135 and 136 of any of the deceleration ring arrangements 132 of the deceleration system 100 shown in FIG. 1. This arrangement minimizes the effect that the fringe electric field lines at the spaces of the split-ring deceleration rings can have on a charged droplet. Hence, as shown in FIG. 6, the spaces 228 and 230 in deceleration ring 134 are oriented at 90° or about 90° from the spaces 232 and 234 in deceleration ring 135. Similarly, the spaces 232 and 234 in deceleration ring 135 are oriented at 90° (or about 90° ) from the spaces 236 and 238 in deceleration ring 135. This orientation continues throughout the entire length of the deceleration ring arrangement 132 as can be appreciated from FIG. 1.

Figure 7:
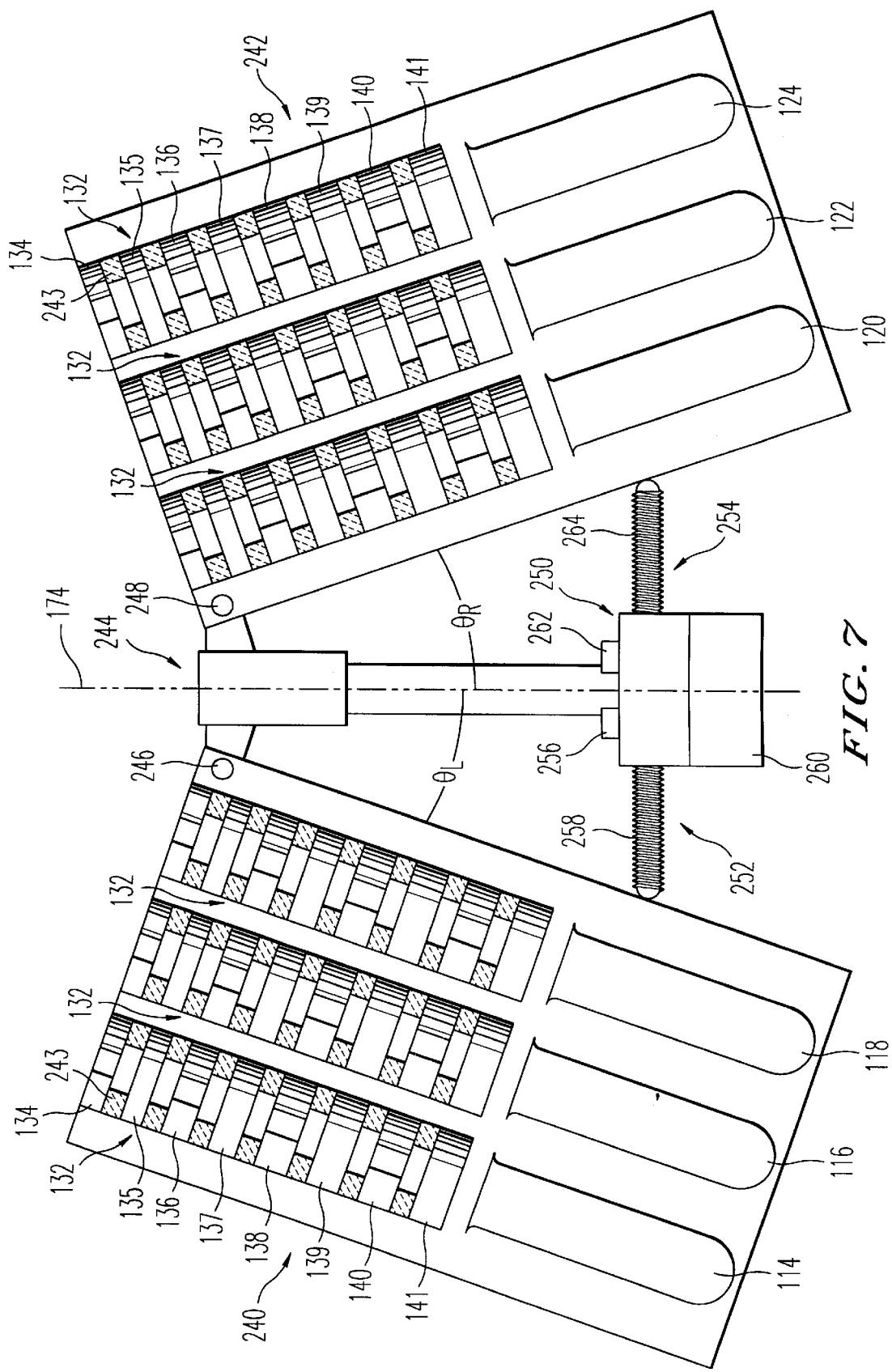
FIG. 7 is a schematic illustration of an apparatus in which the positions of the deceleration elements and collection vessels can be adjusted.

FIG. 7 illustrates an example of a structure in which the deceleration ring arrangement 132 and collection vessels negative 114–124 of FIG. 1 can be housed. In this example, the deceleration ring arrangements 132 associated with collection vessels 114, 116 and 118 are housed with their respective collection vessels in a mounting structure negative 240. Similarly, the deceleration ring arrangements 132 associated with collection vessels 120, 122 and 124 are housed in mounting structure 242. Adjacent deceleration rings 134–141 are spaced from each other by dielectric spacers 243. The mounting structures 240 and 242 are pivotally mounted to a support bar 244 by pivots 246 and 248, respectively. An angle adjusting mechanism 250 having worm gear arrangements 252 and 254 can be used to adjust the angles θL and θR at which the mounting structures 240 and 242, respectively, are angled with respect to the center line 174.

The knob 256 of worm gear arrangement 252 can be turned to cause the worm gear 258 to move further out toward the mounting structure 240 or further into the block 260 of the angle adjusting mechanism 250. If the worm gear 258 is moved further in the direction of mounting structure 240, the worm gear 258 pushes the mounting structure 240 to cause the mounting structure 240 to pivot about pivot 246, thus increasing the magnitude of angle θL. Alternatively, if the worm gear 258 is received further into block 260, the weight of mounting structure 240 will cause it to pivot in an opposite direction about pivot 246, thus decreasing the magnitude of angle θL. Similarly, the knob 262 can be turned to move the worm gear 264 to cause mounting structure 242 to pivot about pivot 248, thus increasing or decreasing the magnitude of angle θR. The angles θL and θR can be changed to better align the deceleration ring arrangements 132 and their corresponding collection vessels 114–124 with the paths 162–172, respectively, along which charged droplets 150–160, respectively, are directed to travel.

Figure 8:
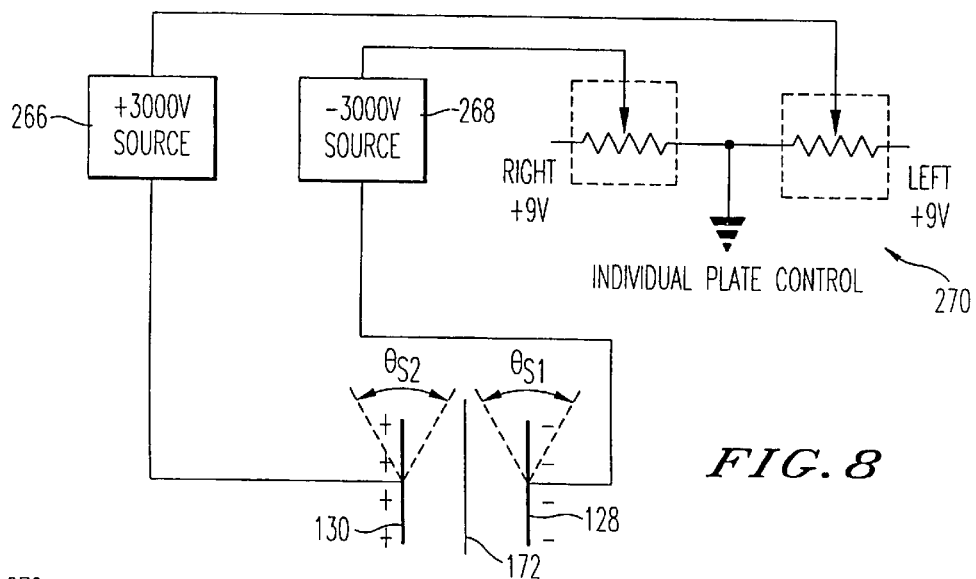
FIG. 8 is a schematic diagram of a circuit for applying the potentials to the steering plates to generate an electrostatic field between the steering plates.

FIG. 8 is a schematic diagram of a circuit for applying selected potentials to the steering plates (e.g., steering plates 128 and 130). The circuit includes two power supplies 266 and 268 which can be controlled by a power supply controller 270, such as a voltage balance circuit. The power supply controller 270 independently controls the power supply 266 to produce a DC output voltage ranging from 0 to +3000 volts, and controls power supply 268 to output a DC voltage ranging from 0 to −3000 volts. For exemplary purposes, the power supplies 266 and 268 are shown connected to the steering plates 128 and 130 of FIGS. 1, 3A and 3B.

Specifically, power supply 266 is coupled to terminal 226 of steering plate 130 to apply a positive voltage ranging from 0 to +3000 volts to steering plate 130. Power supply 268 is coupled to terminal 224 of steering plate 128 to apply a negative voltage ranging from 0 to −3000 volts to steering plate 128. This difference in potential creates an electric field $E_a$ as shown in FIG. 3B between the steering plates 130 and 128. As described in more detail below, the magnitudes of the voltages provided by power supplies 266 and 268 are changed as appropriate to direct the charged droplets (e.g., charged droplet 160) into the deceleration ring arrangement 132 associated with the steering plates 128 and 130. Furthermore, the steering plates 128 and 130 can be angled at angles θ51 and θ52, respectively, as desired with respect to the path (e.g., path 172) along which the charged droplets being directed to a corresponding collection vessel (e.g., vessel 124) travel. By adjusting the angle θ51 and θ52, respectively, the steering plates 128 and 130 are angled with respect to the path of travel of the charged droplets, the steering plates 128 and 130 can better direct the charged droplets into the associated deceleration ring arrangement 132.

Figure 9:
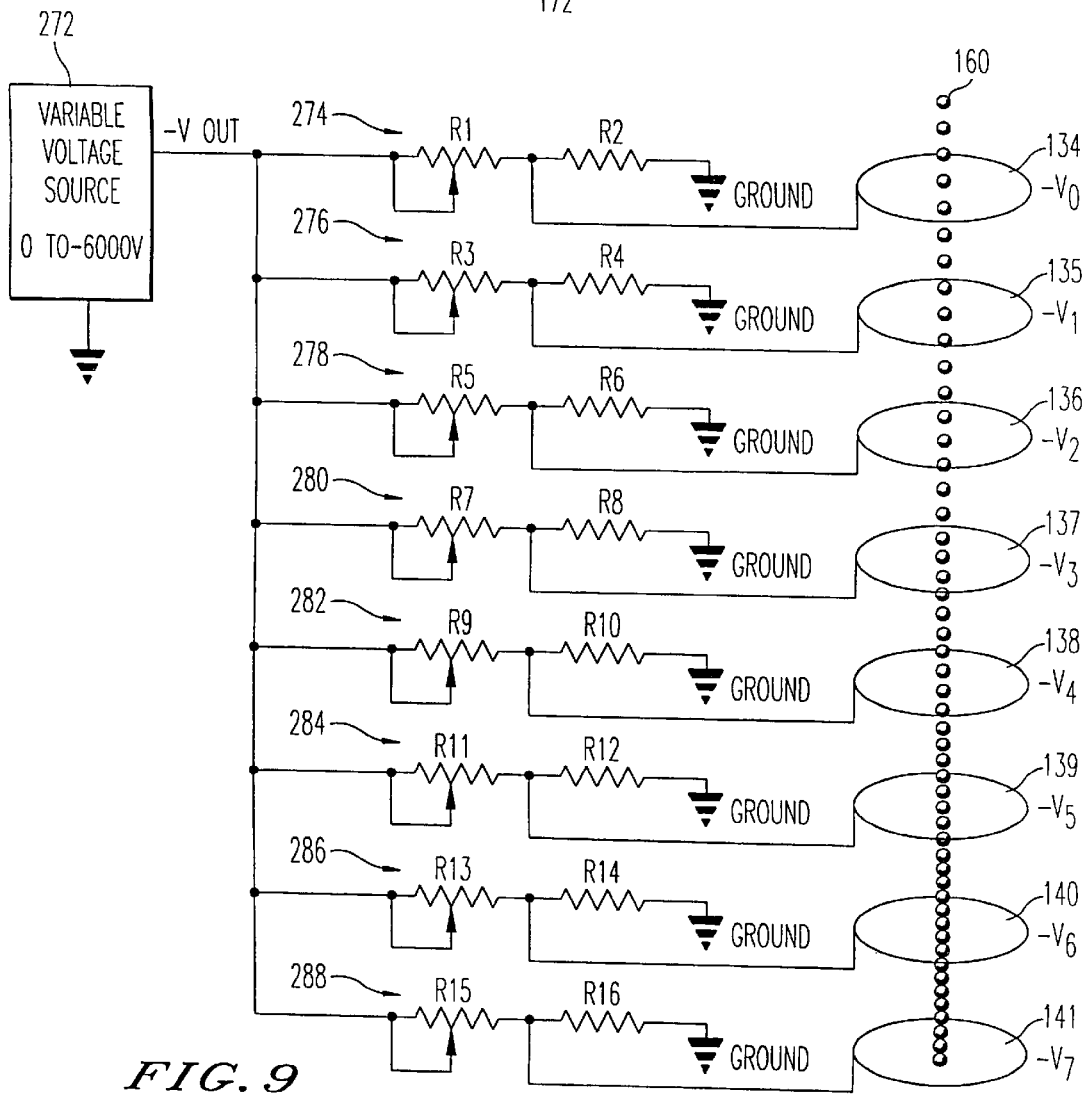
FIG. 9 is a schematic diagram of a circuit for applying selected potentials to the deceleration rings.

FIG. 9 is a schematic diagram of a circuit for applying selected potentials to the deceleration rings of the deceleration ring arrangements 132 and 207. The circuit includes a power supply 272 which can be a DC power supply capable of producing an output voltage within a range from 0 to 6000 volts. The output voltage is adjusted as desired to apply the desired potentials to the deceleration rings. For exemplary purposes, the power supply 272 is shown as applying a range of negative DC voltages $V_0$ through $V_7$ to the deceleration rings 134–141, respectively, of a deceleration ring arrangement 132 that is used to decelerate a negatively charged droplet (e.g., droplet 160). However, as explained in more detail below, the power supply 272 can be configured to apply a range of positive DC voltages to the deceleration rings 134–141 of a deceleration ring arrangement 132 that is used to decelerate positively charged droplets (e.g., droplets 150, 152 or 154).

The circuit of FIG. 9 includes a plurality of voltage dividers 274, 276, 278, 280, 282, 284, 286 and 288 which apply selected potentials to deceleration rings 134–141, respectively. As described above, a deceleration ring arrangement 132 or 207 can include any number of deceleration rings necessary to decelerate the charged droplet by the appropriate amount to prevent damage to the cell contained in the charged droplet. The deceleration ring arrangements 132 or 207 of the deceleration system 100 can include the appropriate amount of deceleration rings which are applied with the appropriate magnitudes of electrical potentials to sufficiently decelerate droplets which have been ejected from the nozzle of the flow cytometer at a sheath fluid pressure of up to about 100 psi so that the cells contained in those droplets are not damaged due to contact with the interior of the collection vessels. The voltage divider 274 includes resistors R1 and R2, voltage divider 276 includes resistors R3 and R4, voltage divider 278 includes resistors R5 and R6, voltage divider 280 includes resistors R7 and R8, voltage divider 282 includes resistors R9 and R10, voltage divider 284 includes resistors R11 and R12, voltage divider 286 includes resistors R13 and R14, and voltage divider 288 includes resistors R15 and R16. As illustrated, the values of the resistors R1–R16 are set to apply a desired potential to the corresponding deceleration rings 134–141. Also, as shown, resistors R1, R3, R5, R7, R9, R11, R13 and R15 are variable resistors whose resistance values can be adjusted to adjust the magnitude of the potential applied to their respective deceleration rings 134–141. The magnitude of the potential applied to each deceleration ring is larger for the rings further away from the topmost deceleration ring 134.

As shown in FIGS. 4A through 6 and described above, when a charged droplet is present in an opening in a deceleration ring, the potential applied to that deceleration ring applies a repulsive electrostatic force to a charged droplet charged to an opposite polarity. The magnitude of the electrostatic force applied to the droplet is proportional to the potential applied to the deceleration ring. Hence, the deceleration rings having a larger potential will exert a larger force on the charged droplet.

The operation of a deceleration system according to the invention will now be described. For exemplary purposes, deceleration system 100 shown in FIG. 1 will be considered. However, the deceleration system 176 shown in FIG. 2 operates in essentially the same manner.

As shown in FIG. 1 and described above, the flow cytometer generates an electric field between the plates 146 and 148 to direct charged droplets toward the appropriate collection vessel 114–124. The deceleration system 100 can be controlled by the flow cytometer to position the steering plate arrangements 126, the deceleration ring arrangements 132, and the collection vessels 114–124 at the appropriate locations so that the charged droplets 150–160 will be directed along paths 162–172, respectively, to pass between the steering plates 128 and 130 of the corresponding steering plate arrangements 126, through the deceleration rings 134–141 in the corresponding deceleration ring arrangements 132, and into the appropriate vessels 114–124. For exemplary purposes, the effect of the deceleration system 100 on the droplet 150 will be discussed.

The steering plate arrangement 126, deceleration ring arrangement 132 and collection vessel 124 for collecting droplets having a negative charge magnitude similar to that of droplet 160 are arranged so that the path 172 along which such droplets will travel essentially aligns with the center points between the steering plates 128 and 130 of the corresponding steering plate arrangement 126 and the center points of deceleration rings 134–141 of the corresponding deceleration ring arrangement 132. As the negatively charged droplet 160 begins to pass between steering plates 128 and 130 of the corresponding steering plate arrangement 126, the electrostatic field $E_a$ (see FIG. 3B) generated between the steering plates 128 and 130 influences the trajectory of the droplet 160. That is, the electrostatic field $E_a$ will impose a force on the droplet 160 to adjust the path 172 along which the droplet 160 is traveling as necessary to direct the droplet 160 into the deceleration ring arrangement 132, so that the droplet 160 enters the first deceleration ring 134 at or near the center point of the deceleration ring 134.

As shown, for example, in FIG. 4A, the potential applied to the deceleration ring 134 will exert an electrostatic force on the droplet 160. Because the droplet is charged at a polarity the same as the polarity of the voltage applied to the ring 134, the force will repel the droplet 160 and thus decrease the speed at which the charged droplet 160 is traveling by a proportionate amount. However, the force will not be sufficient to reverse the direction of movement of the charged droplet 160.

Figure 10A:
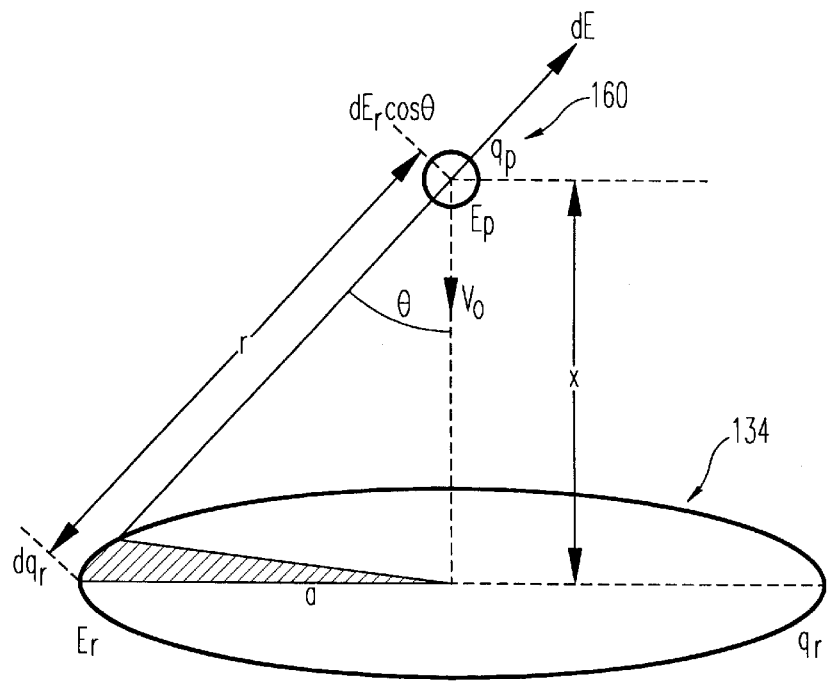
FIGS. 10A and 10B are schematic diagrams illustrating an example of the effect of an electrostatic field generated by a deceleration ring on a charged droplet approaching the deceleration ring.
Figure 10B:
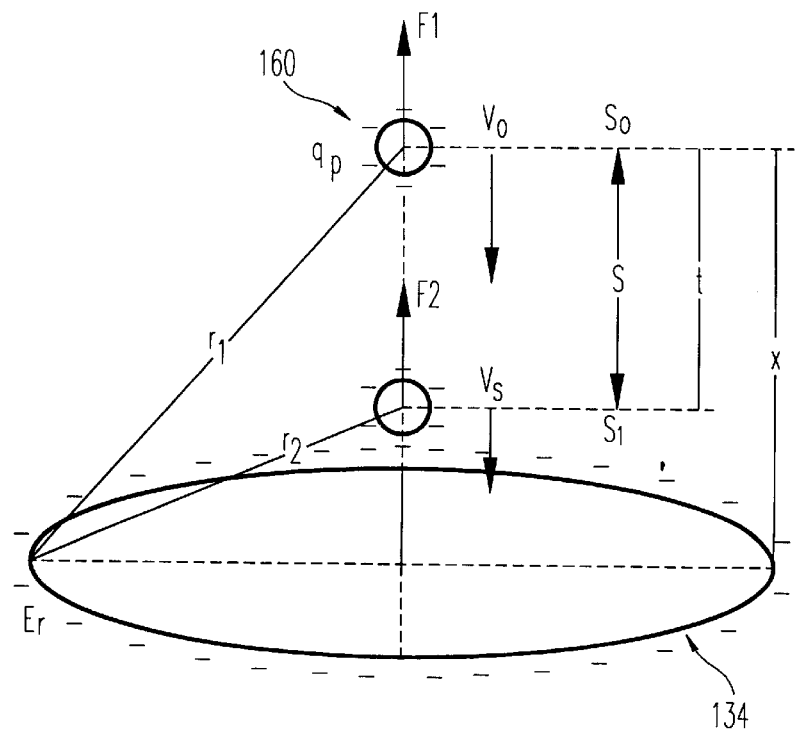

This phenomenon can be further appreciated from the schematic illustrations shown in FIGS. 10A and 10B and the following equations. Specifically, FIGS. 10A and 10B illustrate an example of the effect that an electrostatic field generated by a deceleration ring (e.g., deceleration ring 134) has on a charged droplet (e.g., charged droplet 160) as the charged droplet approaches the deceleration ring.

The field potential $E_r$ of the deceleration ring having a magnitude of charge $q_r$ is calculated as follows:

$$E_r = \int dE \cos\theta = \int \frac{k \cos\theta \, dq}{r^2} = k q_r \frac{x}{(a^2+x^2)^{3/2}} \qquad \text{Equation (1)}$$

with
- k=permitivity constant of space between the droplet 160 and the deceleration ring 134
- x=effective distance between the plane of the deceleration ring 134 and the center of the droplet 160;
- a=the effective radius of the ring On the other hand, the field potential on the droplet 160 is:

$$E_p = V \pi r \qquad \text{Equation (2)}$$

with
- V=voltage at which the droplet 160 is charged; and
- r=radius of the droplet 160.

The change in velocity of the droplet 160 can be best described in accordance with the following equation as it relates to FIG. 10B:

$$V_F = V_O + at \qquad \text{Equation (3)}$$

with
- $V_O$=velocity of droplet 160 at location $S_0$ from deceleration ring 134;
- $V_F$=velocity of droplet 160 at location $S_1$ from deceleration ring 134;
- a=acceleration; and
- t=time for the droplet to travel a distance S Since the acceleration is negative because the charge on the droplet 160 has the same polarity (e.g., "−") as the charge on the deceleration ring 134, equation (3) becomes:

$$V_F = V_0 - at \qquad \text{Equation (4)}$$

The acceleration "a" can be calculated in accordance with the following equation:

$$\int_{S_0}^{S_1} F = Ma = \int_{S_0}^{S_1} \frac{E p E r}{x^2} = E p E r \qquad \text{Equation (5)}$$

with
- m=mass of the droplet; and
- x=effective distance from the droplet to the plane of the deceleration ring 134.

Since $ma = E_p E_r$, the acceleration is:

$$a = \frac{E p E r}{m} \qquad \text{Equation (6)}$$

Hence, inserting this calculated acceleration value into equation (4) above, the velocity $V_p$ of the droplet 160 at point $S_p$ from the deceleration ring 134 is:

$$V_F = V_0 - \frac{(E p E r) t}{m} \qquad \text{Equation (7)}$$

The droplet 160 will then continue along path 172 into the next adjacent deceleration ring 135. In a manner similar to deceleration ring 134, the voltage applied to deceleration ring 135 will apply a repulsive electrostatic force to the charged droplet 160, which decelerates the droplet by an amount proportionate to the force. Because the potential $V_1$ applied to deceleration ring 135 is larger than potential $V_0$ applied to deceleration ring 134, as shown in FIG. 9, the charged droplet 160 will be decelerated by a larger amount.

The charged droplet 160 will then pass into deceleration ring 136, and the potential applied to deceleration ring 136 will exert a repulsive electrostatic force on charged droplet 160 to further slow its movement by a proportionate amount. As the droplet 160 continues to move through the subsequent deceleration rings 137–141, the charged droplet 160 will be decelerated by an amount proportionate to the voltage applied to each of those rings. Accordingly, when the droplet 160 passes out of the last deceleration ring 141 in the deceleration ring arrangement 132, the speed of the charged droplet 160 is significantly less than the speed of the charged droplet 160 at the time it entered the deceleration ring arrangement 132. The slower moving charged droplet 160 will then be collected in the corresponding collection vessel 124. Because the droplet speed has been decreased by the deceleration ring arrangement 132, the force at which the droplet 160 strikes the interior surface of the collection vessel 124 will not be large enough to damage the cell contained in the droplet.

The process continues for all of the droplets having a magnitude of negative charge equal to that of droplet 160. That is, all droplets having that magnitude of negative charge will be deflected by plates 146 and 148 of the flow cytometer to travel along path 172. Because the decelerator ring arrangement 132 slows the speed of these droplets, the individual droplets traveling along path 172 begin to recombine into a continuous stream of sheath fluid and cells prior to entering the corresponding collection vessel 124. Most importantly, the speed at which the cells enter the collection vessel 124 is slow enough so that the cells do not become damaged when they strike the walls of the vessel 124. Also, the centering of the droplets by the steering plate arrangements with respect to their respective deceleration ring arrangements 132 causes the droplets to enter their respective collection vessels centrally or substantially centrally of the vessels.

A similar process is performed by the steering plate arrangements 126 and corresponding deceleration ring arrangements 132 associated with each of the remaining paths 162–170. As discussed above, because the droplets traveling along paths 162, 164 and 166 are positively charged, the voltage supply 272 will apply positive potentials to the deceleration rings 134–141 of the corresponding deceleration ring arrangement 132. The positively and negatively charged droplets having charge magnitudes equal to charged droplets 150–160 can therefore be collected in their corresponding collection vessels 114–124 by the above process without damaging any of the cells contained in those droplets. The collection vessels 114–124 containing the cells can then be removed from the flow cytometer, and the cells can be further analyzed, processed or used as desired.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A device for influencing movement of an electrically charged droplet that has passed through an electric field, the device comprising:
   a conductive element system disposed at a location traversed by the droplet after the droplet passes through the electric field; and
   a potential source which applies at least one electrical potential to the conductive element system, said electrical potential influencing the movement of the droplet when the droplet traverses the conductive element system to selectively decelerate the droplet.

2. A device as claimed in claim 1, wherein:
   the potential source applies the at least one electrical potential to the conductive element system such that the at least one electrical potential influences the path of movement of the droplet.

3. A device as claimed in claim 1, wherein:
   the potential source applies the at least one electrical potential to the conductive element system such that the at least one electrical potential influences the speed of movement of the droplet.

4. A device as claimed in claim 1, wherein:
   the conductive element system comprises a first conductive element arrangement and a second conductive element arrangement; and
   the potential source is adaptable to apply a first potential to the first conductive element arrangement to influence the path of movement of the droplet, and a second potential to the second conductive element arrangement to influence the speed of movement of the droplet.

5. A device as claimed in claim 4, wherein:
   the potential source applies the second potential to the second conductive element arrangement to decelerate the droplet.

6. A device as claimed in claim 1, wherein:
   the conductive element system comprises a pair of conductive elements between which the droplet passes; and
   the potential source is adaptable to apply the potential to the conductive element system as a potential difference between the conductive elements in the pair, so that the potential difference influences the path of movement of the droplet.

7. A device as claimed in claim 1, wherein:
   the conductive element system comprises first and second pairs of conductive elements disposed such that the droplet passes between the conductive elements of the first pair and subsequently passes between the conductive elements of the second pair; and
   the potential source applies said potential to the conductive element system as first and second potential differences between the conductive elements in the first and second pairs, respectively, so that the first and second potential differences and influence the path of movement of the droplet.

8. A device as claimed in claim 1, wherein:
   the conductive element system comprises at least one conductive element having an opening therein, adaptable to allow passage of the droplet therethrough; and
   the potential source applies the potential to the conductive element system as a respective potential for each said conductive element, to influence the speed of movement of the droplet.

9. A device as claimed in claim 8, wherein:
   the respective potential of each said conductive element has a polarity the same as the polarity at which the droplet is charged, in order to repel the droplet and thereby decrease the speed of movement of the droplet.

10. A device as claimed in claim 9, wherein:
    the respective potential of any said conductive element is different from that of any other said conductive element.

11. A device as claimed in claim 8, wherein:
    at least one said conductive element comprises a plurality of sections, spaced from each other and configured to form said opening.

12. A device as claimed in claim 8, wherein:
    the conductive element system comprises a plurality of said conductive elements, disposed in succession from a first said conductive element to a last said conductive element, such that the droplet passes successively through the openings in the conductive elements in a direction from the first to the last said conductive element.

13. A device as claimed in claim 12, wherein:
    the voltage source applies said potential to the conductive element system as a respective potential for each of said conductive elements, with the respective potentials increasing successively such that the respective potential of the first said conductive element is the smallest and the respective potential of the last said conductive element is the largest.

14. A device as claimed in claim 12, wherein:
    the conductive element system further comprises dielectric spacers which are disposed between adjacent said conductive elements.

15. A device for influencing movement of a plurality of electrically charged droplets that have passed through an electric field, the device comprising:
    a plurality of conductive element systems, each disposed at a respective location traversed by any of said droplets after said droplets pass through the electric field; and
    a potential source which applies a respective at least one electrical potential to each of the conductive element systems, each said respective at least one electrical potential influencing the movement of any of the droplets that traverses its respective conductive element system to selectively decelerate the droplet.

16. A device as claimed in claim 15, wherein:
    the plurality of conductive elements systems are relocatable to different respective locations which are to be traversed by any of said droplets after passing through the electric field.

17. A device as claimed in claim 15, wherein:
the potential source applies the respective at least one electrical potential to the conductive element systems such that each said respective at least one electrical potential influences the path of movement of any of the droplets that traverses its respective conductive element system.

18. A device as claimed in claim 15, wherein:
the potential source applies the respective at least one electrical potential to the conductive element systems such that each said respective at least one electrical potential influences the speed of movement of any of the droplets that traverses its respective conductive element system.

19. A device as claimed in claim 15, wherein:
at least one of the conductive element systems comprises a first conductive element arrangement and a second conductive element arrangement; and
the potential source is adaptable to apply a first potential to the first conductive element arrangement of said at least one conductive element system to influence the path of movement of any of the droplets that traverses the first conductive element arrangement, and a second potential to the second conductive element arrangement of said at least one conductive element system to influence the speed of movement of any of the droplets that traverses the second conductive element arrangement.

20. A device as claimed in claim 15, wherein:
at least one of the conductive element systems comprises a pair of conductive elements between which any of the droplets pass; and
the potential source applies the respective potential to said at least one conductive element system as a potential difference between the conductive elements in the pair, so that the potential difference influences the path of movement of any of the droplets traversing the pair.

21. A device as claimed in claim 15, wherein:
at least one of the conductive element systems comprises first and second pairs of conductive elements disposed such that any of the droplets passes between the conductive elements of the first pair and subsequently passes between the conductive elements of the second pair; and
the potential source applies the respective potential to said at least one conductive element system as first and second potential differences between the conductive elements in the first and second pairs, respectively, so that the first and second potential differences each influences the path of movement of any of the droplets.

22. A device as claimed in claim 15, wherein:
at least one of the conductive element systems comprises at least one conductive element having an opening therein, adaptable to allow passage of any of the droplets therethrough; and
the potential source applies the respective potential to said at least one conductive element system as a respective voltage for each said at least one conductive element, to influence the speed of movement of any of the droplets.

23. A device as claimed in claim 22, wherein:
the respective potential of each said conductive element has a polarity the same as the polarity at which said any of the droplets are charged, in order to repel and thereby decrease the speed of movement of said any of the droplets.

24. A device as claimed in claim 23, wherein:
the respective potential of any said conductive element is different from that of any other said conductive element.

25. A device as claimed in claim 22, wherein:
at least one said conductive element comprises a plurality of sections, spaced from each other and configured to form said opening.

26. A device as claimed in claim 22, wherein:
said at least one conductive element system comprises a plurality of said conductive elements, disposed in succession from a first said conductive element to a last said conductive element, such that any of the droplets passes successively through the openings in the conductive elements in a direction from the first to the last said conductive elements.

27. A device as claimed in claim 26, wherein:
the voltage source applies the respective potential to said at least one conductive element system as a respective potential for each of said conductive elements, with the respective potentials increasing successively such that the respective potential of the first said conductive element is the smallest and the respective potential of the last said conductive element is the largest.

28. A device as claimed in claim 26, wherein:
said at least one conductive element system further comprises dielectric spacers which are disposed between adjacent said conductive elements.

29. A method for influencing movement of an electrically charged droplet that has passed through an electric field, comprising the steps of:
placing a conductive element system at a location to be traversed by the droplet after the droplet passes through the electric field; and
applying at lest one electrical potential to the conductive element system to cause the conductive element system to create an electrostatic force which influences the movement of the droplet to selectively decelerate the droplet.

30. A method as claimed in claim 29, wherein:
the potential applying step applies the at least one electrical potential to the conductive element system to create the electrostatic force such that it influences the path of movement of the droplet.

31. A method as claimed in claim 29, wherein:
the potential applying step applies the at least one electrical potential to the conductive element system to create the electrostatic force such that it influences the speed of movement of the droplet.

32. A method as claimed in claim 30, further comprising the steps of:
placing a second conductive element system at a location to be traversed by the droplet after its path of movement has been influenced by the electrostatic force; and
applying at least one second electrical potential to the second conductive element system to cause the second conductive element system to create a second electrostatic force which influences the speed of movement of the droplet.

33. A method as claimed in claim 32, wherein:
the step of applying the at least one second electrical potential causes the second conductive element system to create the second electrostatic force such that the second electrostatic force decelerates the speed of movement of the droplet.

* * * * *